United States Patent
Wu et al.

(10) Patent No.: US 9,324,172 B2
(45) Date of Patent: Apr. 26, 2016

(54) METHOD OF OVERLAP-DEPENDENT IMAGE STITCHING FOR IMAGES CAPTURED USING A CAPSULE CAMERA

(71) Applicant: Capso Vision, Inc., Saratoga, CA (US)

(72) Inventors: Chenyu Wu, Sunnyvale, CA (US); Yi Xu, Menlo Park, CA (US); Kang-Huai Wang, Saratoga, CA (US)

(73) Assignee: Capso Vision Inc., Saratoga, CA (US)

( * ) Notice: Subject to any disclaimer, the term of this patent is extended or adjusted under 35 U.S.C. 154(b) by 0 days.

(21) Appl. No.: 14/675,744

(22) Filed: Apr. 1, 2015

(65) Prior Publication Data

US 2015/0221116 A1 Aug. 6, 2015

Related U.S. Application Data

(63) Continuation-in-part of application No. PCT/US2014/038533, filed on May 19, 2014.

(60) Provisional application No. 61/828,653, filed on May 29, 2013.

(51) Int. Cl.
*G06K 9/00* (2006.01)
*G06T 11/60* (2006.01)
*A61B 1/00* (2006.01)
*A61B 1/04* (2006.01)

(52) U.S. Cl.
CPC .............. *G06T 11/60* (2013.01); *A61B 1/00009* (2013.01); *A61B 1/041* (2013.01); *G06T 2207/10068* (2013.01); *G06T 2207/20221* (2013.01); *G06T 2207/30004* (2013.01)

(58) Field of Classification Search
USPC ........................................................ 382/154
See application file for complete search history.

(56) References Cited

U.S. PATENT DOCUMENTS

| | | | | |
|---|---|---|---|---|
| 5,986,668 A | * | 11/1999 | Szeliski | G06T 7/0028 345/634 |
| 5,987,164 A | * | 11/1999 | Szeliski | G06K 9/209 345/582 |
| 6,009,190 A | * | 12/1999 | Szeliski | G06K 9/209 345/427 |
| 6,018,349 A | * | 1/2000 | Szeliski | G06T 3/0068 345/629 |
| 6,081,278 A | * | 6/2000 | Chen | G06T 17/00 345/473 |
| 6,097,854 A | * | 8/2000 | Szeliski | G06K 9/209 345/634 |
| 6,157,747 A | * | 12/2000 | Szeliski | G06K 9/209 345/419 |

(Continued)

OTHER PUBLICATIONS

"Image Alignment and Stitching: A Tutorial", by Szeliski, Microsoft Research Technical Report MSR-TR-2004-92, Dec. 10, 2006.

*Primary Examiner* — Alex Liew
(74) *Attorney, Agent, or Firm* — Blairtech Solution LLC (57) ABSTRACT

A method of processing images captured by an in vivo capsule camera is disclosed. The images having large overlap exceeding a threshold are stitched into larger images. If the current image and none of its neighboring images has large overlap, the current image is designated as a non-stitched image. Any image, that exists between two images stitched and is not included in the stitched image, is also designated as a non-stitched image. The large-overlap stitching can be performed on the images iteratively by treating the stitched images and non-stitched image as to be processed images in the next round. A second stage stitching can be applied to stitch small-overlap images. The small-overlap image stitching can also be applied iteratively. A third stage stitching can be further applied to stitch the output images from the second stage processing.

26 Claims, 3 Drawing Sheets

(56) References Cited

U.S. PATENT DOCUMENTS

| | | | | |
|---|---|---|---|---|
| 6,359,617 B1* | 3/2002 | Xiong | G06T 3/0068 | 715/848 |
| 6,434,265 B1* | 8/2002 | Xiong | G06K 9/32 | 382/154 |
| 2007/0031062 A1* | 2/2007 | Pal | G06F 17/30843 | 382/284 |
| 2009/0231447 A1* | 9/2009 | Paik | G01S 3/7864 | 348/208.4 |
| 2011/0141226 A1* | 6/2011 | Stec | G06T 3/4038 | 348/36 |
| 2011/0141227 A1* | 6/2011 | Bigioi | G06T 7/0075 | 348/36 |
| 2011/0141300 A1* | 6/2011 | Stec | G06T 3/4038 | 348/222.1 |
| 2012/0019613 A1* | 1/2012 | Murray | H04N 13/0007 | 348/36 |
| 2012/0019614 A1* | 1/2012 | Murray | H04N 13/0007 | 348/36 |

\* cited by examiner

METHOD OF OVERLAP-DEPENDENT IMAGE STITCHING FOR IMAGES CAPTURED USING A CAPSULE CAMERA

CROSS REFERENCE TO RELATED APPLICATIONS

The present invention is a continuation-in-part of PCT Patent Application, Serial No. PCT/US14/38533, filed on May 19, 2014, which claims priority to U.S. Non-provisional Patent Application Ser. No. 61/828,653, filed on May 29, 2013.

FIELD OF THE INVENTION

The present invention relates to reducing time and efforts of examining images captured by an in vivo capsule camera. The large number of images are intelligently stitched into larger images to reduce the number of images.

BACKGROUND AND RELATED ART

Capsule endoscope is an in vivo imaging device which addresses many of problems of traditional endoscopes. A camera is housed in a swallowable capsule along with a radio transmitter for transmitting data to a base-station receiver or transceiver. A data recorder outside the body may also be used to receive and record the transmitted data. The data primarily comprises images recorded by the digital camera. The capsule may also include a radio receiver for receiving instructions or other data from a base-station transmitter. Instead of using radio-frequency transmission, lower-frequency electromagnetic signals may be used. Power may be supplied inductively from an external inductor to an internal inductor within the capsule or from a battery within the capsule. In another type of capsule camera with on-board storage, the captured images are stored on-board instead of transmitted to an external device. The capsule with on-board storage is retrieved after the excretion of the capsule. The capsule with on-board storage provides the patient the comfort and freedom without wearing the data recorder or being restricted to proximity of a wireless data receiver.

The images and data after being acquired and processed are usually displayed on a display device for a diagnostician or medical professional to examine. However, each image only provides a limited view of a small section of the GI tract. It is desirable to form (stitch) a single composite picture with a larger field of view from multiple capsule images. A large picture can take advantage of the high-resolution large-screen display device to allow a user to visualize more information at the same time. An image stitching process may involve removing redundant overlapped areas between images so that a larger area of the inner GI tract surface can be viewed at the same time in a single composite picture. In addition, a large picture can provide a complete view or a significant portion of the inner GI tract surface. It should be easier and faster for a diagnostician or a medical professional to quickly spot an area of interest, such as a polyp. Moreover, captured images may have, for example, 30,000 frames. It will take users more than one hour for review. An image stitching process can thus reduce frame numbers and accelerate the review procedure.

However tissues in the GI tract often deform. Also the capsule movement inside the GI track is not steady. The camera may rotate and hesitate inside the human GI tract. In addition, while the GI tract is supposedly cleaned well before administering the capsule, various objects such as food residues and bubbles may still appear in the images. Therefore, the images captured by the capsule camera are non-ideal from the image models used in various image composition or image stitching processing. It is desirable to develop methods that take into consideration of the fact that the captured images are non-ideal and improve the processing or algorithm convergence speed. For example, if a method can reliably stitch certain types of images, it would reduce the total number to be processed images. Furthermore, if another method can be developed to reliably stitch another type of images, the total number of images to be processed is further reduced.

SUMMARY OF INVENTION

A method of processing images captured using an in vivo capsule camera is disclosed. The images captured by an in vivo capsule camera usually are in large quantity. Examination by a medical professional may take extensive time to complete the task, which will increase the healthcare cost. The present invention first stitches images that can be reliably stitched. In one embodiment, the images having large overlap exceeding a threshold are stitched into larger images so that the number of images is reduced. Furthermore, the larger images imply that larger areas of the corresponding scenes (e.g., the gastrointestinal track of a human body) can be viewed at the same time. As an example, if the degree of picture overlap between a current image and one of neighboring N1 images is larger than a first threshold, the two images are stitched, where N1 is a positive integer. If the degree of picture overlap between the current image and none of its neighboring N1 images is larger than the first threshold, the current image is designated as a non-stitched image. In addition, if any image exists between two images stitched and is not included in the stitched image, the image is also designated as a non-stitched image. The large-overlap stitching can be performed iteratively by treating the stitched images and non-stitched image as to be processed images in the next round. The iteration of large-overlap stitching can be performed until no images can be stitched or a stop criterion is reached.

The large-overlap stitching can be followed by small-overlap stitching to further stitch images generated from the large-overlap stitching. For small-overlap stitching, two images will be stitched only if the degree of picture overlap between the current image and one of the neighboring N2 images is below a second threshold, where N2 is a positive integer. The small-overlap stitching process is similar to the large-overlap stitching. The small-overlap stitching process can be applied iteratively until no more images can be stitched or a certain stop criterion is reached.

After the large-overlap stitching process and the small-overlap stitching process are complete, the system may further apply third-stage image stitching to the stitching results from the small-overlap stitching. A system may also only use the small-overlap stitching.

During large-overlap stitch or small-overlap stitching process, after a current image is stitched with a matched image having either large overlap or small overlap, the stitched images may be treated as a new image replacing the current image and the matched image. Further stitching can be applied to the new image for large-overlap or small-overlap stitching with one of neighboring N1 or N2 images of the matched image during the same iteration of image stitching. Alternatively, no further stitching for the stitched images is applied in the same iteration of image stitching.

The iterative stitching process can be terminated if a stop criterion is asserted. For example, if the stitched image reached a maximum size, no more stitching will be applied to this stitched image. The maximum size may correspond to a maximum picture width or a maximum picture height. In another example, after a maximum number of images are stitched together into a stitched image, no more stitching will be applied to this stitched image. Furthermore, when there is no more image can be stitched, the process will stop.

The indices of stitched images and image model parameters associated with image stitching can be stored along with the original images without the need to store stitched images. During the stitching process, determining the images that can be stitched and determining the model parameters for stitching are computationally intensive. However, after the indices of stitched images and model parameters are determined, the process to generate the stitched images for viewing based on the indices of stitched images and model parameters derived can be performed efficiently. Therefore, with the indices of stitched images and model parameters pre-computed, a low-cost device such as a personal computer or laptop can be used by an end-user to display the stitched images for viewing and examination.

The degree of overlap can be determined based on global transformation of two images. Furthermore, the global transformation can be estimated by exhaustive search for intensity-based image matching between two images. After two images are stitched, local transformation can be applied to the overlapped image areas. The local transformation may include free-form deformation cubic B-splines. Image model parameters required for generating stitched images can be optimized using a gradient-based process.

DETAILED DESCRIPTION OF THE INVENTION

In the following description, various aspects of the present invention will be described. For purposes of explanation, specific configurations and details are set forth in order to provide a thorough understanding of the present invention. Well known features may be omitted or simplified in order not to obscure the present invention.

A review of general technical approaches to image registration and stitching can be found in "Image Alignment and Stitching: A Tutorial", by Szeliski, Microsoft Research Technical Report MSR-TR-2004-92, Dec. 10, 2006.

In image registration, corresponding features, objects or areas from two images are detected and identified first. The two images can then be aligned by warping one image to another according to some mathematical models. Model parameters have to be calculated from the captured images.

Two images may also be registered directly in the pixel domain. The pixel-based registration is also called direct match, which compares the similarity of two image areas based on the image intensity. There are several similarity measurements that can be used for evaluating the quality of pixel-based registration, such as sum of squared distance (SSD), normalized cross correlation (NCC), mutual information (MI), etc. To match images from two different modalities, the mutual information of images A and B is defined as:

$$I(A, B) = \sum_{a,b} p(a, b) \log\left(\frac{p(a, b)}{p(a)p(b)}\right). \tag{1}$$

The mutual information measures the distance between the joint distribution of the images intensity values p(a,b) and the joint distribution with independent the images, p(a)p(b). The MI is a measure of dependence between two images. The underlying assumption for MI is that there is a maximal dependence between the intensity values of the images when they are correctly aligned. Mis-registration will result in a decrease in the measure of mutual information. Therefore, larger mutual information implies more reliable registration.

Image registration based on features extracted from images is another popular approach to the image registration. The feature-based registration first determines a set of feature points in each image and then compares the corresponding feature descriptors. To match two image patches or features captured from two different camera positions or two different viewing angles, an affine camera model including scaling, rotation, etc. is estimated based on the correspondences. To match two images captured at two different camera positions or two different angles, a non-rigid camera model including local deformation can be used.

The number of feature points is usually much smaller than the number of pixels of a corresponding image. Therefore, the computational load for feature-based image registration is substantially less than that for pixel-based image matching. However, it is still time consuming for pair-wise matching. Usually k-d tree, a well-known technique in this field, is utilized to speed up this procedure. Nevertheless, feature-based image registration may not work well for images under some circumstances such as in-vivo images with fewer features. In this case, the direct image registration can serve as a main role and a combination of the above two approaches may be preferred.

Figure 1:
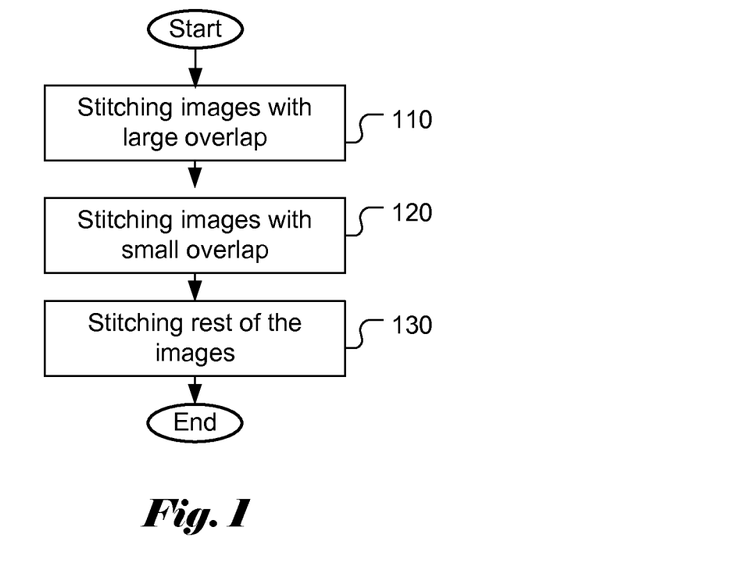
FIG. 1 illustrates an exemplary image sequence stitching consisting of three processing stages for large-overlap images, small-overlap images and the output images from the second stage according to an embodiment of the present invention.

In one embodiment, objects in the scene may deform and lack of distinguishable features. It is very difficult to stitch a set of arbitrary images into a big picture, which contain an accurate anatomic context. A grouping strategy is disclosed to categorize images and then apply stitching method step by step to images in different categories. FIG. 1 illustrates an example of three-stage image stitching according to an embodiment of the present invention. In the first stage, redundant images are removed by stitching images with big overlap. In the second stage, the field of view is enlarged by stitching images with small overlap. In the third stage, the rest of images, i.e., output images from the second stage processing, are stitched. While FIG. 1 illustrates an example of an embodiment of the present invention, a person skilled in the art may practice the present invention by rearranging the steps in FIG. 1 without departing from the spirit of the present invention. For example, the second stage can be skipped. In another embodiment, the first stage may be skipped.

When blending is applied, all detected features will be identified and preserved in the stitched image. Images with big overlaps are most likely redundant and, therefore it is very unlikely to lose important features during stitching. On the other hand, stitching images with small overlaps is unlikely to lose important features as well since the blending areas correspond to a very small percentage of entire images. Therefore, by first stitching images with either big overlap or small overlap can help reduce the total number of images yet to be stitched while reducing the risk of losing important features during the stitching process.

Figure 2:
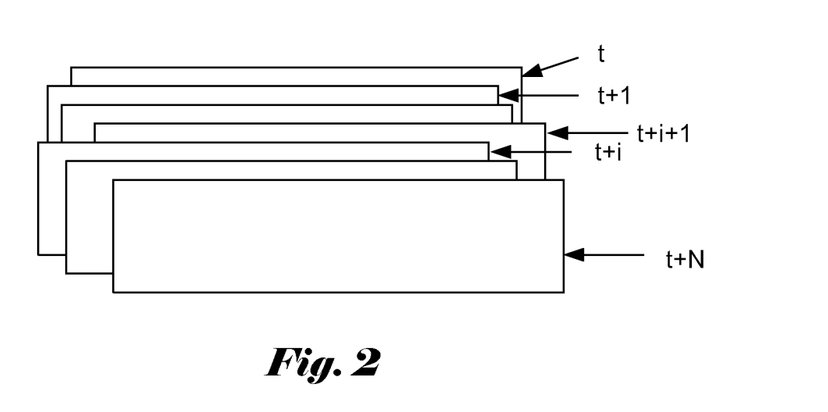
FIG. 2 illustrates an exemplary scenario of images captured by an in vivo camera, where a set of images have a large percentage of overlap.

Due to the peristalsis of the GI tract, the capsule may get stuck and move back and forth at one location for a short period of time and then move to a next location. Therefore a set of images may have a big percentage of overlap, as shown in FIG. 2, where (N+1) images are processed having indices t through t+N covering an area of the GI tract. Due to camera oscillation, the indices of the images may not be sequentially increased from the top image (i.e., index t) to the bottom image (i.e., index t+N). For example, image t+i may be further toward the bottom than image t+i+1.

These images fall into the first category if the overlap exceeds a threshold. For example, the threshold can be set to 80% of overlap with a neighboring image. Therefore, any images sharing big overlap will be stitched together first. To identify these images, a global transformation can be estimated by exhaustively searching for intensity based image matching under the assumption of a global rigid transformation. Once the global transformation is estimated, the overlap between images can be computed. If the degree of overlap satisfies the criteria of first category, a local transformation such as free-form deformation cubic B-splines can be applied to the overlap area. Image model parameters will be required for image stitching. Gradient-based method can be used for optimization of the image model parameters. Finally the deformation field will be extrapolated into the rest of images. In another embodiment, the global transformation can be estimated by averaging the local transformation of individual pixels, while assuming the two images are fully overlapped. The above global transformation estimation is only valid for images with big overlap area.

Various procedures may be used for applying the first stage to a series of images. For example, large-overlap image stitching can be started by checking every two neighboring images. If the pair of images falls into the first category, they are stitched. The stitched image is then treated as a to-be-stitched image for the next round of large overlap stitching and is placed in a to-be-stitched list. After all images are processed for large overlap stitching, a new series of images in the to-be-stitched list is obtained for further stitching. This to-be-stitched list includes images that do not meet the large overlap criterion and stitched image from the previous round of stitching. The large-overlap stitching is performed repeatedly until no neighboring images have large overlap. In other words, the to-be-stitched list becomes empty.

In another embodiment, instead of searching two adjacent images, the neighboring n images can be searched (e.g., n=5) to find the neighboring image with the largest overlap. Due to the camera oscillation, the neighboring image having the largest overlap may not necessarily be an adjacent image, i.e., the immediately neighboring image. For example, the capsule may be in the position X at time t. The camera may move forward during the next frame period (t+1) and move backward in the following frame period (t+2). Therefore, image t+2 may have the largest overlap with image t instead of image t+1. Therefore, if the search window is larger, it is more likely to find a neighboring image with a large overlap.

In the case of multiple neighboring images searched for identifying large overlap, when a neighboring image with large overlap is found, the current image and the neighboring image with large overlap can be stitched. The large overlap stitching process may continue for the stitched image by searching the next n neighboring images. If a large overlap is found between the stitched image and one of the neighboring images, the stitched image is further stitched. If no large overlapped neighboring image is found, the large overlap stitching moves to the next image. The next image may correspond to the image after the current image if the current image cannot be stitched with any of neighboring n image. If a stitched image cannot be further stitched, the next image to be processed corresponds to the image after the last image stitched. For example, if n=5 and image 0 does not have large overlap with any of the next 5 images. Therefore, image 0 is designated as a non-stitched image. If image 1 and image 2 have a large overlap, images 1 and 2 are stitched to form a stitched image (1, 2). The stitched image (1, 2) is then compared with the next 5 neighboring images (i.e., images 3, 4, 5, 6 and 7) to identify any large overlap. If image 5 is found to have a large overlap with stitched image (1, 2), the stitched image (1, 2) is stitched with image 5 to form stitched image (1, 2, 5). If no more image can be stitched with image (1, 2, 5), the large overlap stitching moved to the next image. After image 5 is stitched with image (1, 2), image 3 becomes the first non-stitched image. Therefore, the next image to be processed is image 3. If images 3 and 4 still cannot be stitched with stitched image (1, 2, 5), the stitching process will not be applied to images 3 and 4 in this round. The images between the stitched images, but not included in this stitched image, are designated as non-stitched images. Accordingly, non-stitched images 3 and 4 are designated as non-stitched images. After all images are processed, the large overlap stitching process will output stitched image (1, 2, 5), etc. and non-stitched images 0, 3, 4, etc. The stitched images and non-stitched images are subject to a next round of large overlap stitching. The iteration may be continued until no more images can be stitched. This process may result in a stitched image that grows very big. A stop criterion may be set to stop further stitching if the number of images in the stitched image exceeds a threshold.

In the above example, when two large overlapped images are stitched, the process continues to search the next n un-stitched images for any large overlapped image. Alternatively, when two large overlapped images are stitched (e.g., images 0 and 2), the process outputs the stitched images as a new image (i.e., (0, 2)) and the process moves to the next to-be-processed image, i.e., image 1. The search will determine if image 1 has large overlap with image 3 through image 3+n. Image 2 is not searched in this step since image 2 has already been stitched with image 0. If n=5, and image Shave large overlap with image 1, a stitched image (1, 5) is outputted and the process moved to the next image (i.e., image 3). If there is no large overlap between image 3 and image 4 through image 4+n, image 3 will be designated as non-stitched images. Image 4 becomes the next image to be processed. If no large overlap can be found for image 4, image 4 will be outputted as a non-stitched image. The process will continue until all images are processed. The process will output stitched images (0, 2), (1, 5), etc. and non-stitched images 3, 4, etc. The stitched images and non-stitched images from the process are subject to the next round of large overlap stitching processing. The stitching process is repeated until no more images can be stitched.

In another embodiment, when two or more non-adjacent images with large overlap are stitched, the time stamp (or index) for the stitched image can be computed as a summary of two or more time stamps (or indices). For example, the summary of two or more time stamps can be the average, medium or any individual time stamp, such as example the first one, the middle one or the last one. Alternatively, all individual time stamps can be displayed all together in addition to the stitched image.

A stitched image usually is larger than the original image. Therefore, the composite image (i.e., stitched image) after stitching more images will become larger and larger. However, the display device is limited to a certain size. Therefore, the composite image has to be fitted into the display device. Otherwise the composite image needs to be panned in order to display all parts of the image. Accordingly, the size of the stitched image will be checked and the stitching will be stopped for this composite image if the composite image exceeds the screen size.

The stitched image width can be checked to determine whether the width is close to, equal to or larger than the width of the display window. If so, no further stitching will be performed on this stitched image. Alternatively, the stitched image height can be checked to determine whether the height is close to, equal to or larger than the height of the display window. If so, no further stitching will be performed on this stitched image.

In another embodiment, instead of checking the width or height of the stitched image, the image stitching can also be simply limited to a number of images to be stitched. For example, no more than 10 images can be stitched. If the stitched image already contains 10 images, this composite image will not be further stitched.

After images are stitched in the first stage, the stitched images may be viewed on a display device. The stitching process will result in stitched images larger than the original size. Furthermore, depending on the nature of the original images, each final stitched image may correspond to a different number of original images and have different degrees of overlap. Therefore, the size of final stitched images will vary from image to image. When two stitched images with a large size difference are viewed consecutively, one image may cover a small area on the screen while another may nearly fill up the screen. This would result in very distracting viewing experience. However, in the first stage of stitching, only images with large overlap will be stitched. As a result, the size of the stitched images may not vary too much. It will avoid the potential distracting viewing problem.

Figure 3:
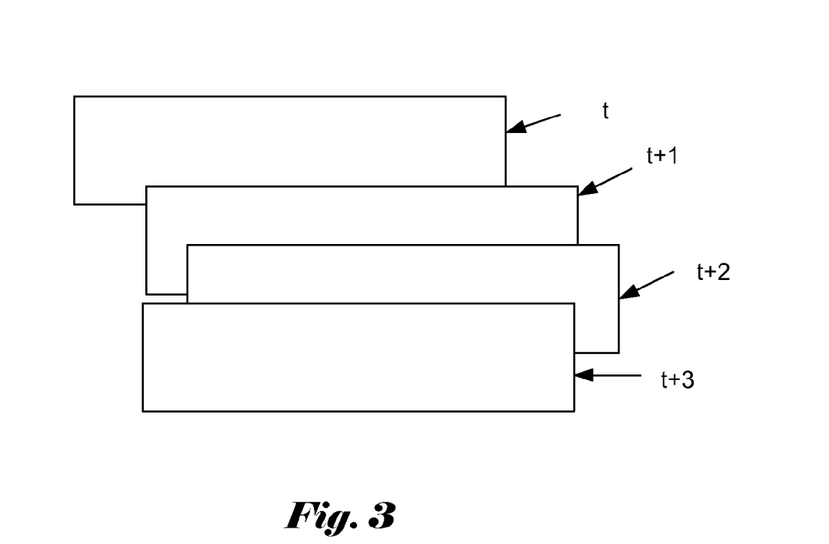
FIG. 3 illustrates an exemplary scenario of images captured by an in vivo camera, where a set of images have a small percentage of overlap.

Once the first stage of stitching is done, the overlap of a current image with neighboring images will be less than a threshold overlap, such as 80%. FIG. 3 illustrates an example of stitched results after the stage 1 stitching, where picture overlap is always less than 80%. Furthermore, the overlap of some neighboring images may be substantially small (e.g., 15% or less as shown between images t and t+1). According to one embodiment of the present invention, the second stage will stitch images with small overlap (i.e., overlap below a low threshold) to generate a composite image with bigger field of view.

In one embodiment, the stitching for images with small overlap is performed using similar procedure as that for the large-overlap stitching. For example, small-over stitching can be started by stitching two neighboring images having small overlap (e.g., 15%). After all images are processed for small-overlap stitching, a new series of images in the to-be-stitched list is obtained for further stitching. This to-be-stitched list includes images that do not meet the small overlap criterion and stitched image from the previous round of stitching. The small-overlap stitching is performed repeatedly until no neighboring images have large overlap. In other words, the to-be-stitched list becomes empty.

To identify these images having small overlap, a global transformation can be estimated by exhaustive search for intensity-based image matching under the assumption of global rigid transformation. Once the global transformation is estimated, the overlap between images can be computed. A local transformation, such as free-form deformation cubic B-splines can be applied to the overlapped area. The model parameters can be optimized by using Gradient-based method. Finally the deformation field will be extrapolated into the rest of images.

In another embodiment, instead of searching the overlap exhaustively in the image, a percentage for expected small overlap, such as 15% can be pre-defined. The intensity based image matching can be applied to fixed area from two adjacent images. For example, 20% image from the bottom of the first image and the top of the second image can be selected. If the matching satisfies certain criteria, such as the NCC matching score being larger than a threshold, these two images do not belong to the small overlap category. They will not be stitched. A high NCC matching score means these two image areas are very similar and these two images are overlapped in the area.

For determining neighboring images with small overlap, a fixed image area for matching can be selected. A rigid transformation model can be applied by searching in both x and y directions within this fixed area in order to find the best overlap area.

During the large-overlap stitching, the size of the composite image (i.e., stitched image) after stitching more images will become larger and larger. Similarly, the size checking process can be applied to the small-overlap procedure. If the stitched size is over a certain size, the small-overlap stitching is not performed to form the stitched image. The stitched image width or height can be checked to determine whether the width or height is close to, equal to or larger than the width or height of the display window. If so, no further stitching will be performed on this stitched image. The number of images stitched can also be checked and no further stitching is applied to a stitched image if the number of images in the stitched image exceeds a limit.

The searching for a small overlapped neighboring image can also be extended to include n neighboring images as for the large overlap stitching. After two images are stitched, the process can search the next n neighboring images of the stitched image for any small overlapped neighboring image similar to the case of large overlap stitching. Alternatively, the stitched images can be outputted as a new image for further stitching in the next stage similar to the case of large overlap stitching.

The stitching of images with small overlap in the second stage of the sequence stitching in FIG. 1 can be performed directly on the original captured images. Since the first stage stitching involves computing local deformation based on optimization, it is computational complicated and consumes a lot of time. It would be a heavy computational burden for a PC based implementation unless the computation is moved to cloud servers. However, this will cause a large amount image data to be uploaded to the cloud server in order to carry out the computations. In order to provide PC-based users the benefits of time-saving viewing of stitched images by reducing the computational requirement, an embodiment identifies images with small overlap from the original captured images.

Figure 4:
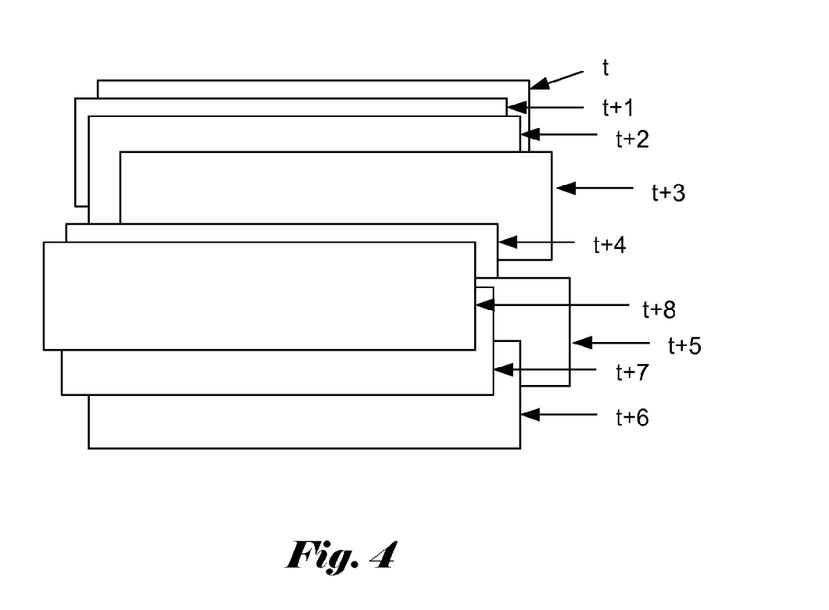
FIG. 4 illustrates an exemplary scenario of images captured by an in vivo camera, where the best matched images may be at some distance way instead of an adjacent image due to camera oscillation.

FIG. 4 illustrates an example of images captured during a camera oscillating while travelling in the GI tract. Therefore, a best match for a current image may not be the immediate neighboring image. Instead, the best match may come from N images away. For example, the overlap between image t+4 and its adjacent image t+3 or t+5 is not large. Instead, the overlap between image t+4 and t+8 is much larger. In practice, the number of neighboring images to be searched to find the best matched overlap may be very large (e.g., N=15). Therefore, the computational load to identify matched images can be very high.

When two or more non-adjacent images with small overlap are stitched, the time stamp for the stitched image can be computed as a summary of two or more time stamps. The summary of two or more time stamps can be average, medium or any individual time stamp for example the first one, the middle one or the last one. Alternatively, all individual time stamps can be displayed all together in addition to the stitched image.

In the image stitching process, to determine what images to be stitched and to determine registration parameters are usually quite computationally intensive. On the other hand, image warping and blending requires relatively low computations if the registration parameters are already known. According to one embodiment, indices of images to be stitched and registration results are computed offline so that the original images can be warped and blended very fast in real time. There is no need to store both original and stitched videos. Instead, the original images, the indices of images to be stitched, and the registration parameters are stored to conserve storage space. In this way, a user can be provided with the option to view the original images or to view the stitched images without the need of intensive computations at the point of use and without the large increase in storage requirement.

According to an embodiment of the present invention, images with large overlap are stitched first. A second stage stitch is applied to the final output from the first stage. In the second stage stitch, images with small overlap are stitched. The final output from the second stage stitch is processed by the third stage stitch. The images to be stitched in the third stage have moderate overlap among them. Therefore, there will be higher risk of losing information during the stitching process. In order to reduce the chance of losing important information, various object detectors, such as bleed detector, tumor detector, etc., are applied to identify suspicious clinical features before the stitching process is applied to these images. After object detection, non-linear matching similar to that in the first two stages of image stitching is applied. The suspicious clinical features are then "inpainted" back to the stitched images if they are blended out during stitching. Accordingly, the risk of losing important information is reduced.

Figure 5:
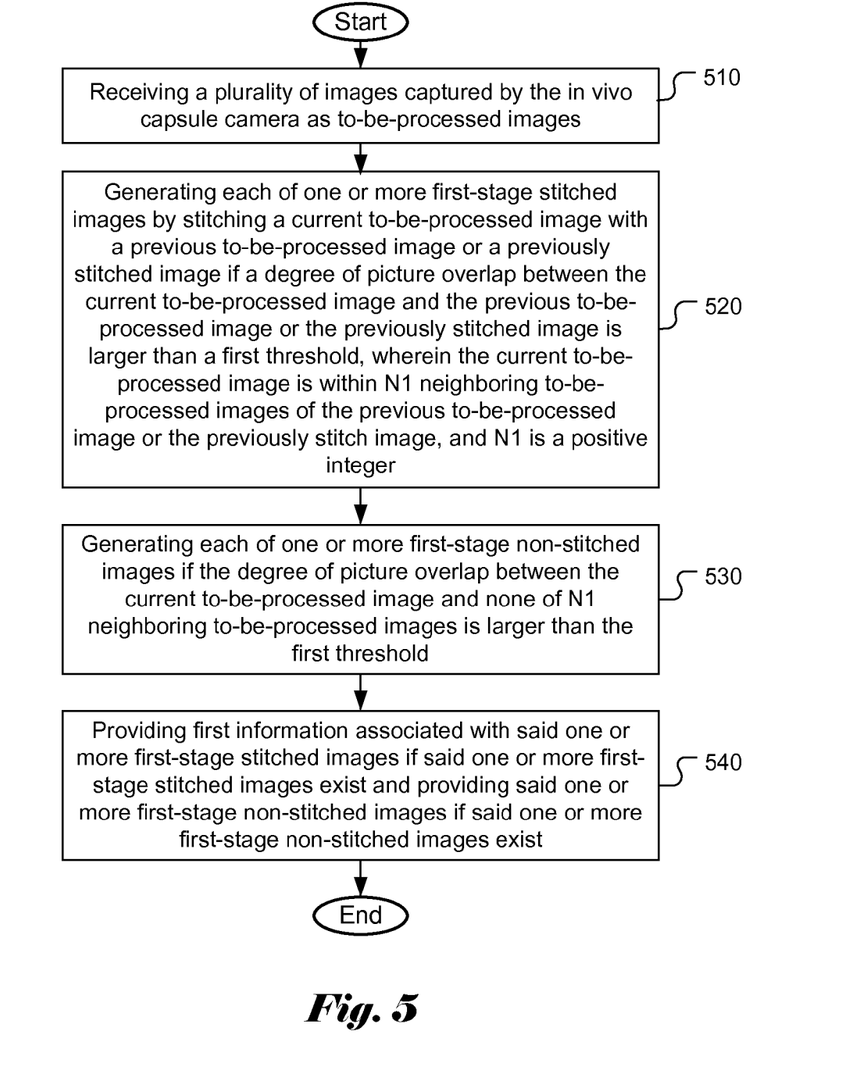
FIG. 5 illustrates an exemplary flowchart for an image sequence stitching system according to an embodiment of the present invention, where images with large overlap are detected and stitched.

FIG. 5 illustrates an exemplary flowchart of a system for image stitching incorporating an embodiment of the present invention. A plurality of images captured by the camera is received as shown in step 510. The images may be retrieved from memory or received from a processor. A first-stage stitched image is generated by stitching a current to-be-processed image with a previous to-be-processed image or a previously stitched image if a degree of picture overlap between the current to-be-processed image and the previous to-be-processed image or the previously stitched image is larger than a first threshold as shown in step 520. The current to-be-processed image is within N1 neighboring to-be-processed images of the previous to-be-processed image or the previously stitch image, and N1 is a positive integer. A first-stage non-stitched images is generated if the degree of picture overlap between the current to-be-processed image and none of N1 neighboring to-be-processed images is larger than the first threshold as shown in step 530. First information associated with said one or more first-stage stitched images is provided in step 540 if said one or more first-stage stitched images exist and providing said one or more first-stage non-stitched images if said one or more first-stage non-stitched images exist.

The invention may be embodied in other specific forms without departing from its spirit or essential characteristics. The described examples are to be considered in all respects only as illustrative and not restrictive. Therefore, the scope of the invention is indicated by the appended claims rather than by the foregoing description. All changes which come within the meaning and range of equivalency of the claims are to be embraced within their scope.

The invention claimed is:

1. A method of processing images captured using an in vivo capsule camera, the method comprising:
    receiving a plurality of images captured by the in vivo capsule camera as to-be-processed images;
    applying large-overlap image stitching to the to-be-processed images, wherein said applying the large-overlap image stitching comprises:
        generating each of one or more first-stage stitched images by stitching a current to-be-processed image with a previous to-be-processed image or a previously stitched image if a degree of picture overlap between the current to-be-processed image and the previous to-be-processed image or the previously stitched image is larger than a first threshold, wherein the current to-be-processed image is within N1 neighboring to-be-processed images of the previous to-be-processed image or the previously stitch image, and N1 is a positive integer; and
        generating each of one or more first-stage non-stitched images if the degree of picture overlap between the current to-be-processed image and none of N1 neighboring to-be-processed images is larger than the first threshold; and
    providing first information associated with said one or more first-stage stitched images if said one or more first-stage stitched images exist and providing said one or more first-stage non-stitched images if said one or more first-stage non-stitched images exist.

2. The method of claim 1, further comprising:
    repeating said large-overlap image stitching by setting said one or more first-stage stitched images and said one or more first-stage non-stitched images as the to-be-processed images in a next first-stage iteration if at least one first-stage stitched image is generated in a current first-stage iteration; and
    terminating said large-overlap image stitching if no first-stage stitched image is generated in the current first-stage iteration.

3. The method of claim 2, after said large-overlap image stitching is terminated, further comprising:
    determining second-stage to-be-processed images consisting of any existing first-stage stitched images and any existing first-stage non-stitched image;
    applying small-overlap image stitching to the second-stage to-be-processed images, wherein said applying the small-overlap image stitching comprises:
        generating each of one or more second-stage stitched images by stitching a current second-stage to-be-processed image with a previous second-stage to-be-processed image or a previously second-stage stitched image if the degree of picture overlap between the current second-stage to-be-processed image and the previous second-stage to-be-processed image or the previously second-stage stitched image is smaller than a second threshold, wherein the current second-stage to-be-processed image is within N2 neighboring second-stage to-be-processed images of the previous second-stage to-be-processed image or the previously second-stage stitched image, and N2 is a second positive integer; and generating each of one or more second-stage non-stitched images if the degree of picture overlap between the current second-stage to-be-processed image and none of N2 neighboring second-stage to-be-processed images is smaller than the second threshold; and providing second information associated with said one or more second-stage stitched images if said one or more second-stage stitched images exist and providing said one or more second-stage non-stitched images if said one or more second-stage non-stitched images exist.

4. The method of claim 3, further comprising:

repeating said small-overlap image stitching by setting said one or more second-stage stitched images and said one or more second-stage non-stitched images as the second-stage to-be-processed images in a next second-stage iteration if at least one second-stage stitched image is generated in a current second-stage iteration; and terminating said small-overlap image stitching if no second-stage stitched image is generated in the current second-stage iteration.

5. The method of claim 4, after said small-overlap image stitching is terminated, further comprising:

determining third-stage to-be-processed images consisting of any existing second-stage stitched images and any existing second-stage non-stitched image;

generating third-stage stitched images by applying general image stitching to the third-stage to-be-processed images; and providing third information associated with the third-stage stitched images.

6. The method of claim 5, wherein said general image stitching comprises detecting clinical features in the third-stage to-be-processed images and inpainting the clinical features detected back into the third-stage stitched images.

7. The method of claim 5, wherein the first information comprises first indices and first image model parameters associated with said one or more first-stage stitched images; the second information comprises second indices and second image model parameters associated with said one or more second-stage stitched images; and the third information comprises third indices and third image model parameters associated with said one or more third-stage stitched images.

8. The method of claim 7, further comprising retrieving the first indices and the first image model parameters associated with said one or more first-stage stitched images, generating said one or more first-stage stitched images based on the first indices and the first image model parameters associated with said one or more first-stage stitched images; retrieving the second indices and the second image model parameters associated with said one or more second-stage stitched images, generating said one or more second-stage stitched images based on the second indices and the second image model parameters associated with said one or more second-stage stitched images; and retrieving the third indices and the third image model parameters associated with said one or more third-stage stitched images, generating said one or more third-stage stitched images based on the third indices and the third image model parameters associated with said one or more third-stage stitched images.

9. The method of claim 4, wherein the first information comprises first indices and first image model parameters associated with said one or more first-stage stitched images, and the second information comprises second indices and second image model parameters associated with said one or more second-stage stitched images.

10. The method of claim 9, further comprising retrieving the first indices and the first image model parameters associated with said one or more first-stage stitched images, generating said one or more first-stage stitched images based on the first indices and the first image model parameters associated with said one or more first-stage stitched images, and retrieving the second indices and the second image model parameters associated with said one or more second-stage stitched images, generating said one or more second-stage stitched images based on the second indices and the second image model parameters associated with said one or more second-stage stitched images.

11. The method of claim 3, wherein if said generating each of said one or more second-stage stitched images by stitching the current second-stage to-be-processed image with the previous second-stage to-be-processed image or the previously second-stage stitched image generates one second-stage stitched image having a horizontal size or a vertical size exceeding a size threshold, said generating each of said one or more second-stage stitched images is skipped.

12. The method of claim 3, wherein the degree of picture overlap between the current second-stage to-be-processed image and the previous second-stage to-be-processed image or the previously second-stage stitched image is determined based on global transformation between the current second-stage to-be-processed image and the previous second-stage to-be-processed image or the previously second-stage stitched image.

13. The method of claim 12, wherein the global transformation is estimated by exhaustive search for intensity-based image matching between the current second-stage to-be-processed image and the previous second-stage to-be-processed image or the previously second-stage stitched image.

14. The method of claim 3, wherein said generating each of said one or more second-stage stitched images by stitching the current second-stage to-be-processed image with the previous second-stage to-be-processed image or the previously second-stage stitched image comprises applying a local transformation to an overlap area of the current second-stage to-be-processed image with the previous second-stage to-be-processed image or the previously second-stage stitched image.

15. The method of claim 14, wherein the local transformation includes free-form deformation cubic B-splines.

16. The method of claim 14, wherein image model parameters required for said generating each of said one or more second-stage stitched images are optimized using a gradient-based process.

17. The method of claim 2, wherein the first information comprises indices and image model parameters associated with said one or more first-stage stitched images after said large-overlap image stitching is terminated.

18. The method of claim 17, further comprising retrieving the indices and the image model parameters associated with said one or more first-stage stitched images, and generating said one or more first-stage stitched images based on the indices and the image model parameters associated with said one or more first-stage stitched images.

19. The method of claim 1, wherein said generating each of said one or more first-stage stitched images from the to-be-processed images comprises applying a local transformation to an overlap area between the current to-be-processed image and the previous to-be-processed image or the previously stitched image.

20. The method of claim 19, wherein the local transformation includes free-form deformation cubic B-splines.

21. The method of claim 19, wherein image model parameters required for said generating each of said one or more first-stage stitched images are optimized using a gradient-based process.

22. The method of claim 1, wherein if said generating each of said one or more first-stage stitched images by stitching the current to-be-processed image with the previous to-be-processed image or the previously stitched image generates one first-stage stitched image having a horizontal size or a vertical size exceeding a size threshold, said generating each of said one or more first-stage stitched images is skipped.

23. The method of claim 1, wherein each first-stage stitched image is generated by stitching the current to-be-processed image with the previous to-be-processed image continuously when the degree of picture overlap between the current to-be-processed image and the previous to-be-processed image or the previously stitched image is larger than the first threshold, and said stitching the current to-be-processed image with the previous to-be-processed image continuously is terminated when a stop criterion is met.

24. The method of claim 23, wherein the stop criterion corresponds to a total number of the to-be-processed images stitched into the first-stage stitched image reaching a threshold or a horizontal size or vertical size of the first-stage stitched image exceeding a threshold.

25. The method of claim 1, wherein each first-stage stitched image is generated by stitching the current to-be-processed image with the previous to-be-processed image and each first-stage stitched image consists of two to-be-processed images.

26. A method of processing images captured using an in vivo capsule camera, the method comprising:
receiving a plurality of images captured by the in vivo capsule camera as to-be-processed images;
applying small-overlap image stitching to the to-be-processed images, wherein said applying the small-overlap image stitching comprises:
generating each of one or more first-stage stitched images by stitching a current to-be-processed image with a previous to-be-processed image or a previously stitched image if a degree of picture overlap between the current to-be-processed image and the previous to-be-processed image or the previously stitched image is smaller than a first threshold, wherein the current to-be-processed image is within N1 neighboring to-be-processed images of the previous to-be-processed image or the previously stitch image, and N1 is a positive integer; and
generating each of one or more first-stage non-stitched images if the degree of picture overlap between the current to-be-processed image and none of N1 neighboring to-be-processed images is smaller than the first threshold; and
providing first information associated with said one or more first-stage stitched images if said one or more first-stage stitched images exist and providing said one or more first-stage non-stitched images if said one or more first-stage non-stitched images exist.

* * * * *